(12) United States Patent
Shinoda

(10) Patent No.: US 6,222,582 B1
(45) Date of Patent: Apr. 24, 2001

(54) IMAGE CAPTURE SYSTEM

(75) Inventor: Tatsuo Shinoda, Mine (JP)

(73) Assignee: Sumitomo Metal (SMI) Electronics Devices Inc., Mine (JP)

( * ) Notice: Subject to any disclaimer, the term of this patent is extended or adjusted under 35 U.S.C. 154(b) by 0 days.

(21) Appl. No.: 09/118,933

(22) Filed: Jul. 20, 1998

(30) Foreign Application Priority Data

Jul. 24, 1997 (JP) .................................................. 9-197673

(51) Int. Cl.⁷ ........................................................ H04N 7/18
(52) U.S. Cl. ............................................... 348/87; 348/126
(58) Field of Search ................................ 348/86, 87, 92, 348/94, 95, 125, 126, 129, 130; 382/203, 286, 284

(56) References Cited

U.S. PATENT DOCUMENTS

| | | | |
|---|---|---|---|
| Re. 35,816 | * 6/1998 | Schulz | 356/376 |
| 5,276,546 | * 1/1994 | Palm et al. | 348/126 |
| 5,841,539 | * 11/1998 | Ikurumi et al. | 356/376 |
| 5,847,833 | * 12/1998 | Yokoyama et al. | 356/375 |
| 5,848,188 | * 12/1998 | Shibata et al. | 382/203 |
| 6,055,054 | * 4/2000 | Beaty et al. | 356/376 |
| 6,057,967 | * 5/2000 | Takahashi et al. | 359/641 |
| 6,064,759 | * 5/2000 | Buckley et al. | 382/154 |

FOREIGN PATENT DOCUMENTS

| | | | |
|---|---|---|---|
| 61-39539 | 2/1986 | (JP) | G01B/11/30 |
| 8-233554 | 9/1996 | (JP) | G01B/11/24 |

* cited by examiner

*Primary Examiner*—Vu Le
(74) *Attorney, Agent, or Firm*—Foley & Lardner

(57) ABSTRACT

An image capture system in which images of a plurality of divided parts of an object are photographed includes at least one movable mirror disposed over the object so as to reflect a part of the object to be photographed, a mirror driver for changing an angle of the movable mirror relative to the object so that the part of the object reflected on the movable mirror is changed to another part of the object to be photographed, a camera for photographing the part of the object reflected on the movable mirror, and an image processor capturing an image signal from the camera every time the angle of the movable mirror is changed. The movable mirror is located a predetermined value or above higher than the object so that the image photographed by the camera is prevented from being unfocused upon angular change of the movable mirror. The movable mirror is preferably located higher than the object by 30 cm or more.

5 Claims, 1 Drawing Sheet

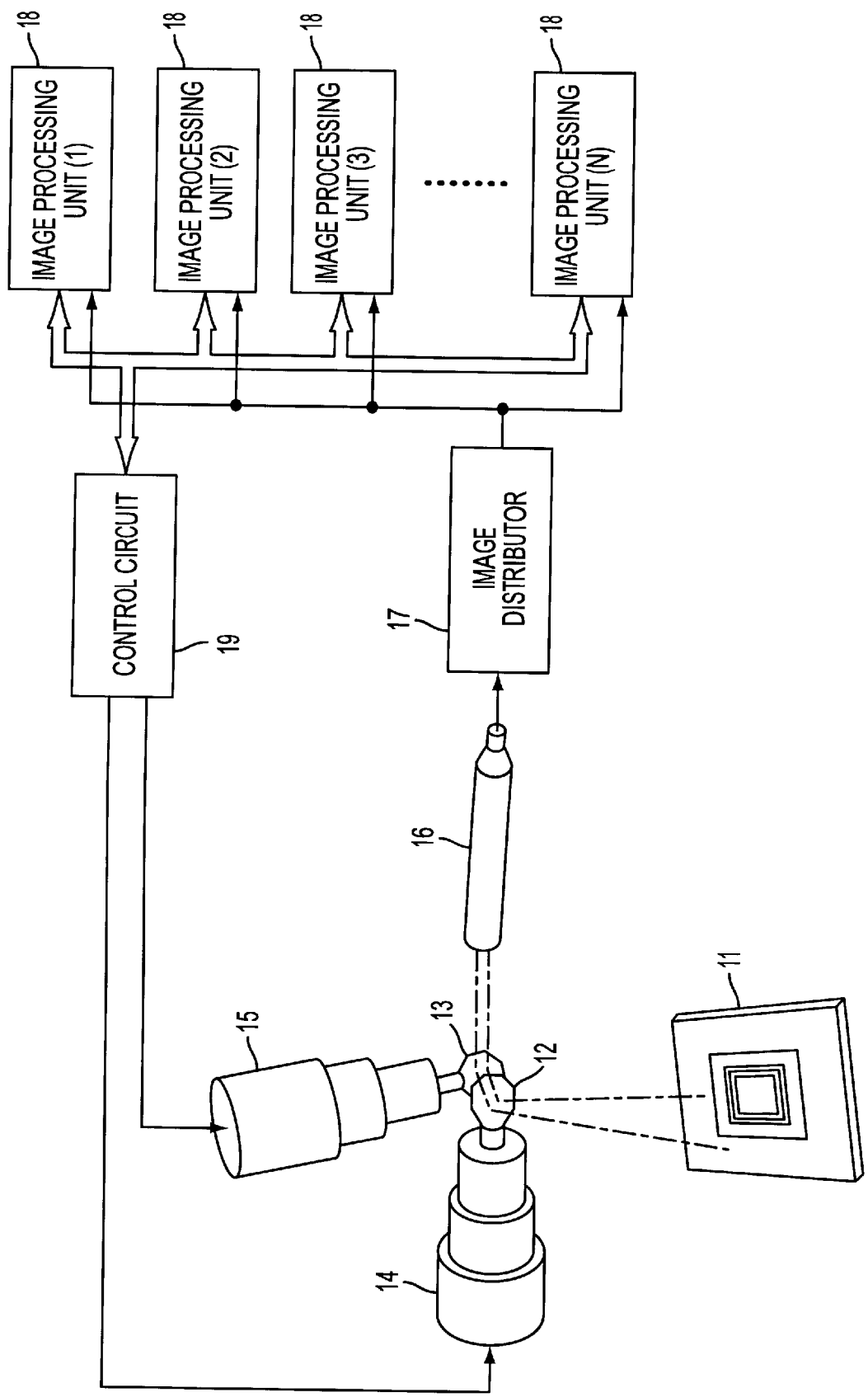

IMAGE CAPTURE SYSTEM

BACKGROUND OF THE INVENTION

1. Field of the Invention

This invention relates to an image capture system for capturing image signals representative of a plurality of divided images of an object photographed by a camera.

2. Description of the Prior Art

An inspection step for circuit substrates is conventionally provided with an inspection system including a camera for photographing wire-bonded parts or portions etc. of a substrate surface, for example. In this inspection system, an image of a minute wire-bonded part is difficult to be recognized when the overall circuit substrate is photographed so as to come into the range of the camera. Accordingly, parts of the circuit substrate to be inspected are photographed as respective enlarged images. The circuit substrate usually includes a plurality of parts to be inspected. The camera or the circuit substrate is moved horizontally so that different parts to be inspected are photographed.

In the above-described inspection system, however, it is difficult to capture images of a plurality of different parts to be inspected at high speeds since moving the camera or the circuit substrate takes much time. Consequently, the above-described inspection system cannot meet the requirement of high speed processing.

To solve the above-described drawback, the prior art has provided a system in which a plurality of cameras are set for each of the parts to be inspected so that images of different parts photographed by the respective cameras are captured. In this system, however, a plurality of cameras cannot be juxtaposed when the parts to be inspected are located near to one another. Accordingly, this system cannot be applied to an inspection system for small components such as the circuit substrates.

Japanese Unexamined Patent Publication No. 8-233554 (1996) discloses a system including two galvanometer mirrors disposed above the object to be inspected. A part of the object is reflected on the galvanometer mirrors in turn, and angles of the galvanometer mirrors relative to the object is switched at a predetermined frequency so that the part of the object to be reflected on the galvanometer mirrors is changed. Two lenses are disposed in front and in the rear of the galvanometer mirrors respectively. Parts of the object reflected on the galvanometer mirrors in turn are sequentially photographed by the camera in synchronization with the changes in the angles of the galvanometer mirrors. Consequently, images of the entire object with a large area can be captured at a high speed.

In the disclosed system, one of the galvanometer mirrors has a wide changing range of its angle (swing angle) for the purpose of photographing an object with a large area. Accordingly, a distance between the part to be photographed and the galvanometer mirror is varied to a large extent with the change in the angle of the galvanometer mirror. This results in variations in the length of an optical path between the part to be photographed and the camera to a large extent. The variations in the length of the optical path result in an unfocused image photographed by the camera. In the disclosed system, the two lenses are disposed in front and in the rear of the galvanometer mirrors respectively to compensate a focal length. However, provision of these lenses complicates the arrangement of the optical system and increases the cost of the system.

SUMMARY OF THE INVENTION

Therefore, an object of the present invention is to provide an image capture system for capturing image signals representative of a plurality of divided images of an object photographed by a camera, wherein the arrangement of the optical system can be simplified.

To achieve the object, the present invention provides an image capture system comprising at least one movable mirror disposed over an object so as to reflect a part of the object to be photographed, a mirror driver for changing an angle of the movable mirror relative to the object so that the part of the object reflected on the movable mirror is changed to another part of the object to be photographed, a control circuit for controlling the mirror driver, a camera for photographing the part of the object reflected on the movable mirror, an image processor capturing an image signal from the camera every time the angle of the movable mirror is changed, and means for locating the movable mirror a predetermined value or above higher than the object so that the image photographed by the camera is prevented from being unfocused upon angular change in the movable mirror. In order that the image photographed by the movable camera may be prevented from being unfocused due to an angular change of the movable mirror, the movable mirror is preferably located higher than the object by 30 centimeters or more.

The movable mirror is located higher than the object so that the swing angle thereof is decreased. The distance between the part of the object to be photographed and the movable mirror varies with the change in the angle of the movable mirror. In the above-described arrangement, however, the variations in the distance are decreased so that the variations in the length of the optical path between the part of the object to be photographed and the camera are reduced. Consequently, the image photographed by the camera is prevented from being unfocused. Furthermore, since the swing angle of the movable mirror is reduced, even the part in the periphery of the object can accurately be photographed at nearly a right angle to the camera.

In a preferred form, the image processor comprises a plurality of image processing units whose number is equal to or smaller than the number of parts of the object to be photographed. The image processing units deliver to the control circuit photographing request signals requesting different parts of the object to be photographed respectively. The control circuit controls the mirror driver in response to the photographing request signal from each image processing unit so that the angle of the movable mirror is changed. The camera photographs the requested part of the object to be photographed after completion of the angular change in the movable mirror, each image-processing unit having delivered the photographing request signal captures an image signal from the camera. Consequently, the image signal representative of an optional part of the object can be captured at high speeds. Furthermore, the image signals representative of a plurality of parts of the object can be processed by a plurality of image processing units in a parallel processing mode respectively. This provides a high speed image processing for the entire object.

In another preferred from, upon completion of the angular change of the movable mirror, the control circuit delivers a ready signal to the image processing unit having delivered the photographing request signal, thereby informing an image signal capture timing. Based on the receipt of the ready signal, each image processing unit can accurately judge the timing for capturing the image signal from the camera.

In further another preferred form, each image processing unit compares the captured image of the object to be photographed with a predetermined reference imager thereby inspecting an appearance and/or dimensions of the photographed part of the object. Alternatively, each image processing unit performs an operation for obtaining at least one of an area, outside dimensions, and coordinates of the captured image of the part of the object, thereby inspecting an appearance and/or dimensions of the photographed part of the object on the basis of results of the operation. In this arrangement, each image processing unit can execute processes from the capture of the image signal to the inspection of each part of the object at high speeds.

Other objects, features and advantages of the present invention will become clear upon reviewing the following description of the preferred embodiment thereof.

BRIEF DESCRIPTION OF THE DRAWINGS

FIGURE illustrates an appearance inspection system of one embodiment in accordance with the present invention.

DETAILED DESCRIPTION OF THE PREFERRED EMBODIMENT

One embodiment of the present invention will be described with reference to the FIGURE. The invention is applied to an appearance inspection system in the embodiment. A circuit substrate 11 to be inspected serves as an object to be photographed. Two movable mirrors, that is, a Y galvanometer mirror 12 and an X galvanometer mirror 13 are disposed above the substrate 11. The galvanometer mirrors 12 and 13 are mounted on rotational shafts of galvano-motors 14 and 15 constituting mirror drivers respectively. A control circuit 19 controls rotation angles of the galvano-motors 14 and 15 to change angles of the galvanometer mirrors 12 and 13, thereby changing a part of the substrate 11 to be photographed. More specifically, a Y-axis location of the part of the substrate 11 to be photographed is determined by the Y galvanometer mirror 12, and an X-axis location thereof is determined by the X galvanometer mirror 13. A two-dimensional camera 16 such as a small-sized CCD camera is disposed ahead of the X galvanometer mirror 13. An image reflected on the X galvanometer mirror 13 is photographed by the camera 16. Thus, the image of the part of the substrate 11 to be inspected is photographed through the Y galvanometer mirror 12 and the X galvanometer mirror 13 in turn by the camera 16.

In order that the image photographed by the camera 16 may be prevented from being unfocused due to changes in an angle of the Y galvanometer mirror 12 relative to the substrate 11, the Y galvanometer mirror 12 is located higher than the substrate 11 to be inspected by a predetermined distance (30 cm, for example) or more. Consequently, a maximum owing angle of the Y galvanometer mirror 12 is set at or less than ±20 degrees.

Image signals delivered from the camera 16 are distributed via an image distributor 17 to a plurality of image processing units 18 constituting an image processor. The number of the image processing units 18 is set to be equal to or smaller than the number of parts to be photographed on the substrate 11. The image signals representative of different parts of the substrate 11 to be photographed are captured by the respective image processing units 18.

The control circuit 19 controlling the galvano-motors 14 and 15 receives photographing request signals delivered from the respective image processing units 18. Based on the received photographing request signal, the control circuit 19 controls the rotation angles of the galvano-motors 14 and 15 to change the angles of the galvanometer mirrors 12 and 13, thereby changing the part of the substrate 11 to be photographed to that required by the image processing unit 18. Upon completion of changing the angles of the galvanometer mirrors 12 and 13, the control circuit 19 delivers a ready signal to the image processing unit 18 requesting the part of the substrate 11 to be photographed, thereby informing an image signal capture timing. Thereafter, the image signal representative of the part of the substrate 11 photographed by the camera 16 is captured by the image processing unit 18 having received the ready signal or having requested the part of the substrate 11 to be photographed.

Each image processing unit 18 processes the captured image signal to thereby obtain an image of the substrate part to be photographed. Each processing unit 18 then compares the image of the part with a predetermined reference image, thereby inspecting an appearance and/or dimensions of the part. A warning lamp, buzzer or the like is actuated when a defective portion such as breakage or disconnection has been detected as the result of the inspection. Furthermore, a defective substrate is automatically excluded into a defective recovery section, and only normal circuit substrates are carried to a next step.

An inspection method should not be limited to the above-described case where the image of the part is compared with the reference image. For example, a gray search may be carried out for the image of the part to obtain a contour or an outline of the part, so that an area inside the contour is operated to be compared with a reference area, or outside dimensions and/or coordinates of the part are operated on the basis of the results of the search to be compared with a reference value.

According to the above-described appearance inspection system, the Y galvanometer mirror 12 is located higher relative to the substrate 11 so that the swing angle thereof is reduced. This reduces the variations in the distance between the part of the substrate 11 to be photographed and the Y galvanometer mirror 12 due to the angular change of the latter, thereby reducing the variations in the length of an optical path between the part to be photographed and the two-dimensional camera 16. Consequently, the image photographed by the camera 16 can be prevented from being unfocused due to the angular change of the Y galvanometer mirror 12. The lenses conventionally provided in front and in the rear of the galvanometer mirrors 12 and 13 for correcting the unfocused image need not be disposed in the above-described system. Consequently, the arrangement of the optical system can be simplified, and the appearance inspection system can be rendered low-cost. Furthermore, since the swing angle of the Y galvanometer mirror 12 is reduced, even a part in the periphery of the substrate 11 can be photographed nearly at right angles to the camera. This can reduce distortion of the photographed image due to differences in the locations of the parts of the substrate 11.

A plurality of image processing units 18 are provided as described above. The number of the image processing units 18 is equal to or smaller than the number of parts of the substrate 11 to be photographed. The image processing units 18 request the different parts of the substrate 11 to be photographed respectively. In response to the request, the control circuit 19 changes the rotation angles of the galvano-motors 14 and 15 to thereby change the angles of the galvanometer mirrors 12 and 13. In this state, the requested part of the substrate 11 is photographed by the camera 16, and the image signal representative of the photographed part is supplied to the image processing unit 16 having requested the part to be photographed. In this arrangement, only 5 msec elapse between the delivery of request for the photographing from the image processing unit 18 and output of the ready signal after completion of the angular changes of the galvanometer mirrors 12 and 13. Consequently, the image signal representative of any part of the substrate to be photographed can be captured at high speeds. Moreover, the image signals representative of a plurality of parts of the substrate can be processed by the respective image processing units 18 in a parallel processing mode. This can provide a high-speed image processing for the overall substrate 11.

An additional image processing unit is provided when a new part to be inspected is added to the substrate 11. The new image processing unit delivers a photographing request signal to the control circuit 19 so that the new part of the substrate 11 is photographed. In this case, too. the image signals representative of a plurality of parts of the substrate can be processed by the respective image processing units 18 in the parallel processing mode. An image processing time for the overall substrate 11 is not extended so excessively and accordingly, the requirement of high-speed processing can be met.

The appearance inspection system is provided with only one two-dimensional camera 16 in the foregoing embodiment. However, a plurality of two-dimensional cameras having different magnifications or visual fields may be provided, instead. In this case, one of the two-dimensional cameras is designated by each image processing unit 18 so that each image processing unit 18 captures the image signal from the designated two-dimensional camera.

Furthermore, when a plurality of two-dimensional cameras are provided, the two-dimensional camera used for the photographing may be changed according to the location of the part of the substrate to be photographed. In this case, when the location of each two-dimensional camera is adjusted by measuring an accurate length of the optical path between each two-dimensional camera and each part of the substrate to be photographed, an unfocused image can reliably be prevented and accordingly, a clear image can be obtained.

A plurality of image processing units 18 are provided in the foregoing embodiment. However, a single image processing unit may process the images of the respective parts of the substrate to be photographed sequentially, instead. Furthermore, the image capture system of the present invention is applied to the appearance inspection system for the circuit substrates in the foregoing embodiment. However, the invention may be used for the positioning of electronic components in a wire bonding step, the positioning of semiconductor packages or in an inspection step for the semiconductor packages.

The foregoing description and drawing are merely illustrative of the principles of the present invention and are not to be construed in a limiting sense. Various changes and modifications will become apparent to those of ordinary skill in the art. All such changes and modifications are seen to fall within the scope of the invention as defined by the appended claims.

What is claimed is:

1. A image capture system comprising:

at least one movable mirror disposed over an object so as to reflect a part of the object to be photographed;

a mirror driver for changing an angle of the movable mirror relative to the object so that the part of the object reflected on the movable mirror is changed to another part of the object to be photographed;

a control circuit for controlling the mirror driver;

a camera for photographing the part of the object reflected on the movable mirror;

an image processor capturing an image signal from the camera every time the angle of the movable mirror is changed, and means for locating the movable mirror at least a predetermined value above the object so that the image photographed by the camera is prevented from being unfocused upon angular change in the movable mirror, and wherein:

the image processor comprises a plurality of image processing units whose number is equal to or smaller than the number of parts of the object to be photographed, the image processing units deliver photographing request signals to the control circuit requesting different parts of the object to be photographed respectively;

the control circuit controls the movable mirror in response to the photographing request signal from each image processing unit so that the angle of the movable mirror is changed; and the camera photographs the requested part of the object to be photographed after completion of the angular change in the movable mirror, each image processing unit having delivered the photographing request signal captures an image signal from the camera.

2. An image capture system according to claim 1, wherein the movable mirror is located higher than the object by 30 centimeters or more.

3. An image capture system according to claim 1, wherein upon completion of the angular change in the movable mirror, the control circuit delivers a ready signal to the image processing unit having delivered the photographing request signal, thereby informing an image signal capture timing.

4. An image capture system according to claim 1, wherein each image processing unit compares the captured image of the part of the object to be photographed with a predetermined reference image, thereby inspecting an appearance and/or dimensions of the photographed part of the object.

5. An image capture system according to claim 1, wherein each image processing unit performs an operation for obtaining at least one of an area, outside dimensions, and coordinates of the captured image of the part of the object, thereby inspecting an appearance and/or dimensions of the photographed part of the object on the basis of results of the operation.

\* \* \* \* \*